United States Patent
Mak et al.

(10) Patent No.: US 10,038,846 B2
(45) Date of Patent: Jul. 31, 2018

(54) SURGICAL CAMERA SYSTEM WITH AUTOMATIC ALTERNATION BETWEEN TWO DEPTHS OF FIELD

(71) Applicants: Siu Wai Jacky Mak, Toronto (CA); Michael Frank Gunter Wood, Toronto (CA); Yanhui Bai, Toronto (CA)

(72) Inventors: Siu Wai Jacky Mak, Toronto (CA); Michael Frank Gunter Wood, Toronto (CA); Yanhui Bai, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/549,804

(22) PCT Filed: Mar. 9, 2015

(86) PCT No.: PCT/IB2015/051704
§ 371 (c)(1),
(2) Date: Aug. 9, 2017

(87) PCT Pub. No.: WO2016/142738
PCT Pub. Date: Sep. 15, 2016

(65) Prior Publication Data
US 2018/0035053 A1    Feb. 1, 2018

(51) Int. Cl.
*H04N 5/232* (2006.01)
*A61B 34/20* (2016.01)
(Continued)

(52) U.S. Cl.
CPC ......... *H04N 5/23245* (2013.01); *A61B 34/20* (2016.02); *A61B 90/37* (2016.02);
(Continued)

(58) Field of Classification Search
CPC . A61B 2034/2057; A61B 34/20; A61B 90/37; G02B 27/0075; H04N 5/23219;
(Continued)

(56) References Cited

U.S. PATENT DOCUMENTS

| 8,937,651 B2 | 1/2015 | Guissin et al. |
| 2001/0012053 A1* | 8/2001 | Nakamura ......... A61B 1/00193 348/45 |

(Continued)

FOREIGN PATENT DOCUMENTS

WO    WO-2016142738 A1    9/2016

OTHER PUBLICATIONS

International Search Report dated Aug. 18, 2017, by ISA, re PCT Patent Application No. PCT/IB2016/057276.
(Continued)

*Primary Examiner* — Francis G Geroleo
(74) *Attorney, Agent, or Firm* — Perry + Currier Inc.

(57) ABSTRACT

A surgical camera system with automatic alternation between two depths of field is provided, comprising: a tunable iris configured to automatically alternate between a first depth of field ("DOF") and a second DOF larger than the first DOF; one or more lenses configured to collect light using the iris; a body containing the iris and at least a portion of the lenses; a sensor configured to produce images from the light; a video processing unit configured to: produce an image stream from first images and second images produced by the sensor from the light, the first images acquired at the first DOF and the second images acquired at the second DOF; and adjust one or more lighting parameters of the first images and the second images prior to producing the image stream; and, a display device in communication with the video processing unit, configured to render the image stream.

13 Claims, 10 Drawing Sheets

(51) Int. Cl.
*A61B 90/00* (2016.01)
*H04N 5/243* (2006.01)
*G02B 27/00* (2006.01)

(52) U.S. Cl.
CPC ..... *G02B 27/0075* (2013.01); *H04N 5/23232* (2013.01); *H04N 5/243* (2013.01); *A61B 2034/2057* (2016.02); *H04N 5/23219* (2013.01)

(58) Field of Classification Search
CPC . H04N 5/23232; H04N 5/23245; H04N 5/243
See application file for complete search history.

(56) References Cited

U.S. PATENT DOCUMENTS

2005/0140820 A1* 6/2005 Takeuchi ............. H04N 13/021
348/362

2013/0338439 A1* 12/2013 Kosugi .............. A61B 1/00193
600/111

OTHER PUBLICATIONS

Examination Report dated Sep. 12, 2017, by CIPO, re Canadian Patent Application No. 2977172.
Written Opinion dated Aug. 18, 2017, by ISA, re PCT Patent Application No. PCT/IB2016/057276.
Zuo. Oct. 7, 1013. High-speed transport-ofOintensity phase microscopy with an electrically tunable lens. Optics Express. vol. 21 (20). pp. 24060-24075.
Grewe. Jul. 1, 2011. Fast two-layer two-photon imaging of neuronal cell populations using an electrically tunable lens. Biomedical Optics Express. vol. 2 (7). pp. 2035-2046.
International Search Report dated Nov. 24, 2015 for International Application No. PCT/IB2015/051704.
Written Opinion dated Nov. 24, 2015 for International Application No. PCT/IB2015/051704.

* cited by examiner

SURGICAL CAMERA SYSTEM WITH AUTOMATIC ALTERNATION BETWEEN TWO DEPTHS OF FIELD

FIELD

The specification relates generally to surgical camera systems and methods for minimally invasive therapy and image guided medical procedures, and specifically to a surgical camera system with automatic alternation between two depths of field.

BACKGROUND

Generally, there is a conflict between acquiring images at both high resolution and large depth of field, for example using a camera. Specifically, the higher resolution, the shallower depth of field. Recently, computing imaging technology has been developed that produces an extended depth of field at higher resolutions, for example the light field camera (which uses either a microlens array on an image sensor or a diffuser component in an optics path to generates a fusion coded image), but because much data is required to construct images from such technologies, processing times are high and are not compatible with video speeds. For surgical techniques, binocular-style cameras, for example, FusionOptics™ technology from Leica™, have been used with a first camera acquiring images at a high resolution and low depth of field, and a second camera acquiring images at a low resolution and high depth of field. The cameras are arranged binocularly so that a surgeon can peer down both cameras with different eyes; the surgeon's brain then constructs a three-dimensional image from the two sets of images, but in general this equipment can be difficult to use for long periods of time due to eye fatigue and the development of headaches.

SUMMARY

The present disclosure is generally directed to image guided medical procedures using an access port and/or open surgery. The port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Further, a surgical camera system is provided that includes a tunable iris that can be controlled between two depths of field, and an image stream is produced from images acquired at each depth of field and output to a display device, for example in a video stream, so that a surgeon can view the image stream with both eyes. At certain frame rates, the image stream can provide a pseudo three-dimensional effect. The two depths of field can be selected to present depth information to a surgeon and guide a surgical tool being imaged by the surgical camera system, when the image stream is provided at video rates. Furthermore, adding imaging processing functions to the surgical camera system can result in further useful information in the image stream rendered at the display device and provided to the surgeon during surgery.

An aspect of the present specification provides a surgical camera system comprising: a tunable iris configured to automatically alternate between a first depth of field and a second depth of field larger than the first depth of field; one or more lenses configured to collect light using the tunable iris; a body containing the tunable iris and at least a portion of the one or more lenses; a sensor configured to produce images from the light received from the one or more lenses and the tunable iris; a video processing unit configured to: produce an image stream from first images and second images produced by the sensor from the light received from the one or more lenses and the tunable iris, the first images acquired at the first depth of field and the second images acquired at the second depth of field; and adjust one or more lighting parameters of the first images and the second images prior to producing the image stream; and, a display device in communication with the video processing unit, the display device configured to render the image stream.

The surgical camera system can further comprise a video buffering unit configured to one or more of buffer and sequence the first images and the second images prior to being streamed by the video processing unit.

The image stream can alternate between images acquired at the first depth of field and the second depth of field.

The image stream can comprise images acquired at the first depth of field and the second depth of field rendered in one or more given sequences.

The first depth of field and the second depth of field can be selected so that the image stream results in a three dimensional effect at the display device when the image streams are rendered thereon.

The first depth of field can be in a range of about 5 mm to about 100 mm.

The second depth of field can be in a range of about 2 mm to about 80 mm.

The second images can have a smaller resolution that the first images.

The surgical camera system can further comprise a reference clock, and the tunable iris can be configured to automatically alternate between the first depth of field and the second depth of field according to a time sequence generated using the reference clock. The first images and the second images can be acquired in association with alternating pulses of the time sequence.

The display device can comprise a heads up display (HUD) device.

The image stream can comprise video frames of a video stream. The video stream can be rendered at the display device at a frame rate that is greater than or equal to about 20 frames per second.

The video processing unit can be further configured to adjust one or more lighting parameters of the first images and the second images prior to producing the image stream by one or more of: balancing respective brightness of one or more of the first images and the second images; balancing respective gain values of one or more of the first images and the second images; and, performing brightness matching on one or more of the first images and the second images prior to producing the image stream.

The body can comprise a proximal end and a distal end, the distal end can be configured for positioning adjacent tissue being imaged by the one or more lenses and the tunable iris.

The body can be configured for use with a surgical port.

The surgical camera system can further comprise a tracking device configured to be tracked by a navigation system.

BRIEF DESCRIPTIONS OF THE DRAWINGS

For a better understanding of the various implementations described herein and to show more clearly how they may be carried into effect, reference will now be made, by way of example only, to the accompanying drawings in which.

Figure 8:
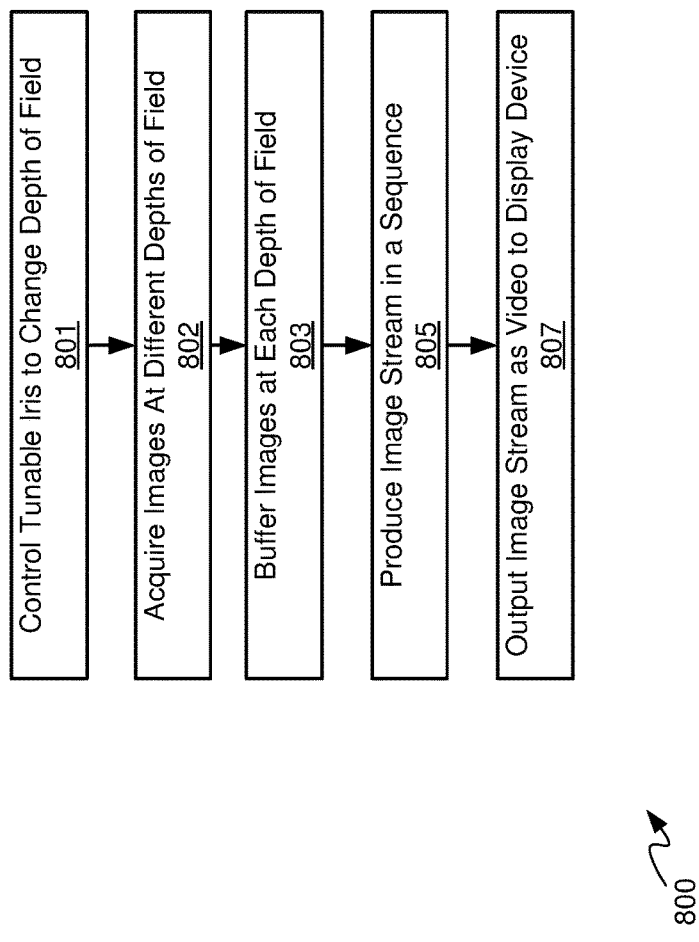

FIG. 8 a block diagram of a method for automatic alternation between two depths of field, according to non-limiting implementations.

Figure 9:
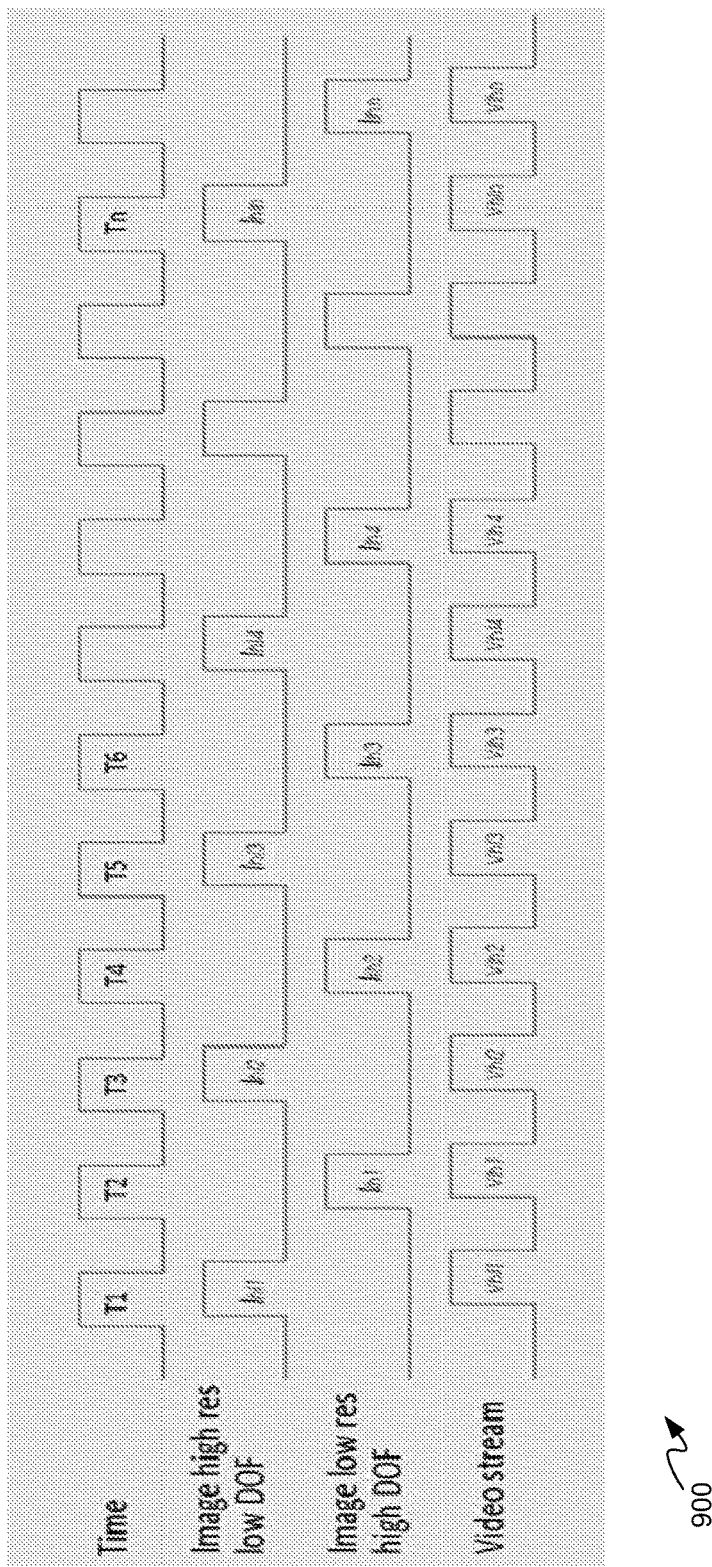

FIG. 9 depicts a time sequence for acquiring images at two depths of field, according to non-limiting implementations.

Figure 6:
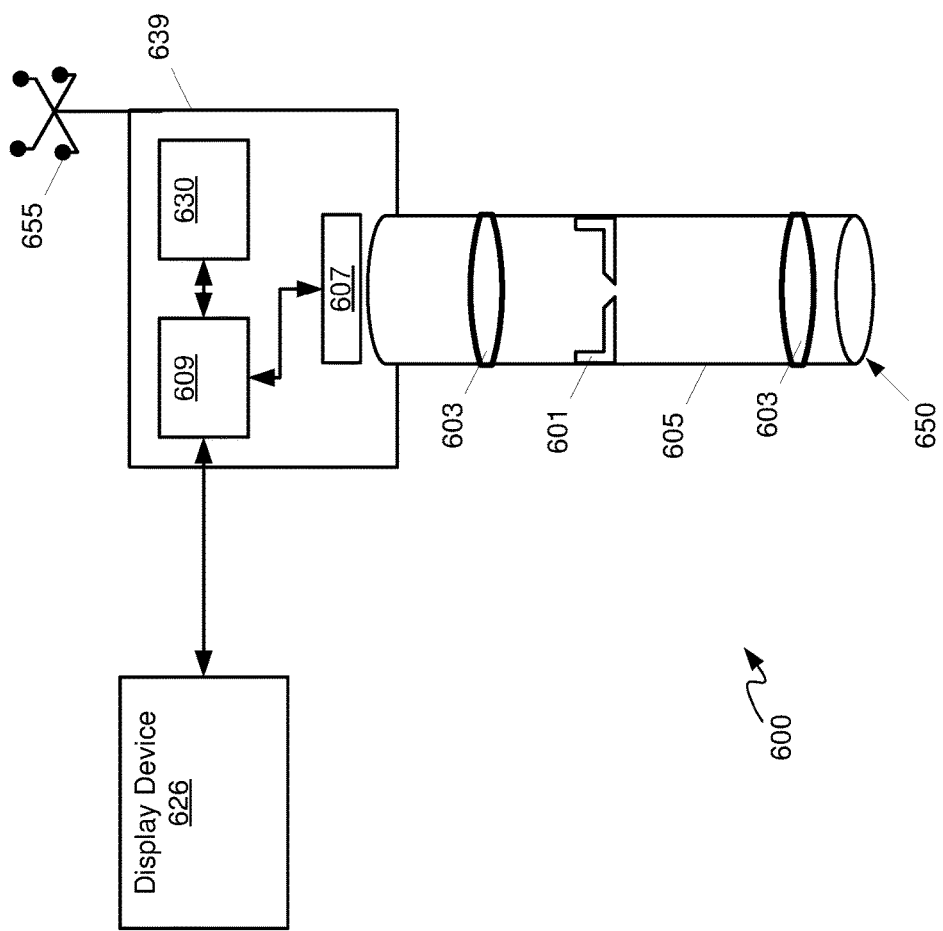
FIG. 6 depicts a schematic diagram of a surgical camera system with automatic alternation between two depths of field, according to non-limiting implementations.
Figure 10:
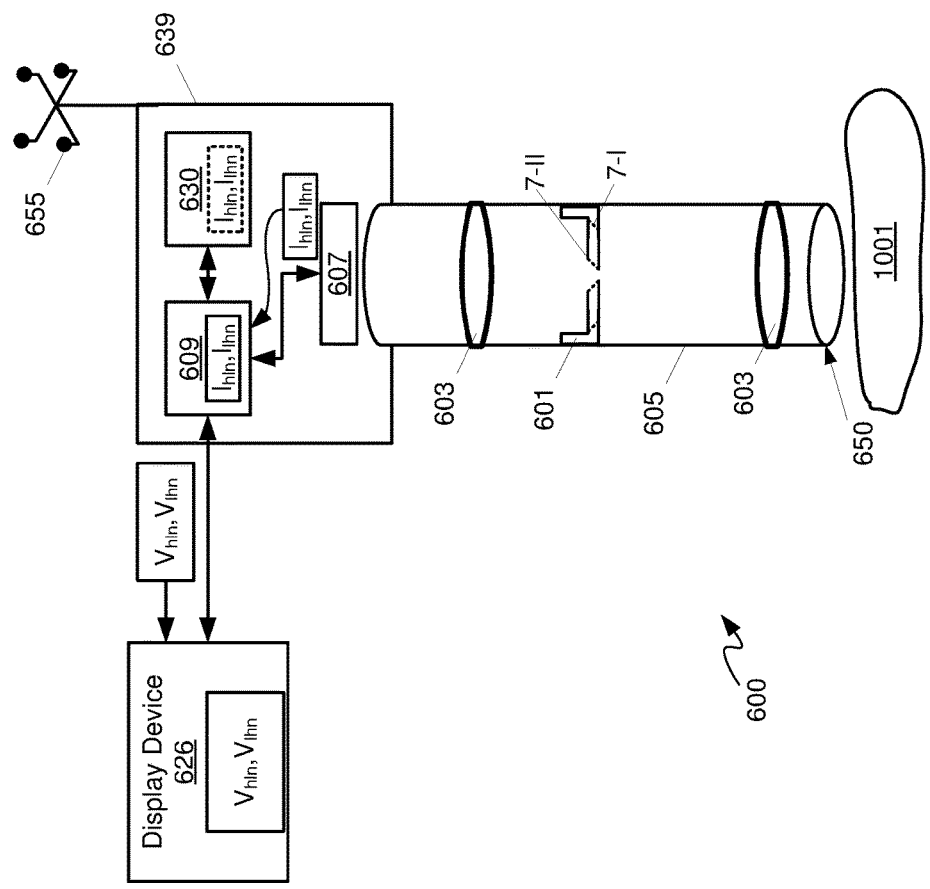

FIG. 10 the system of FIG. 6 in use, according to alternative non-limiting implementations.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
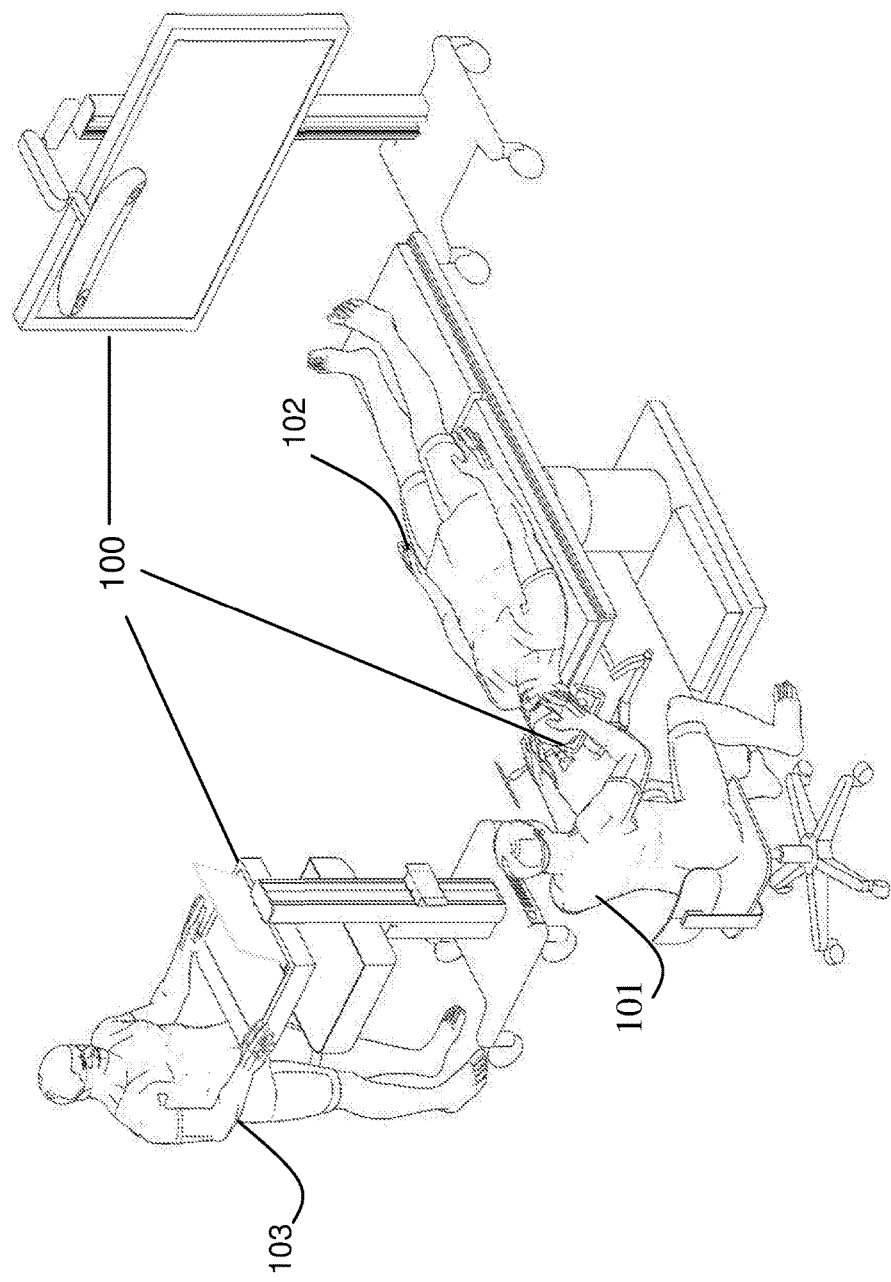
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
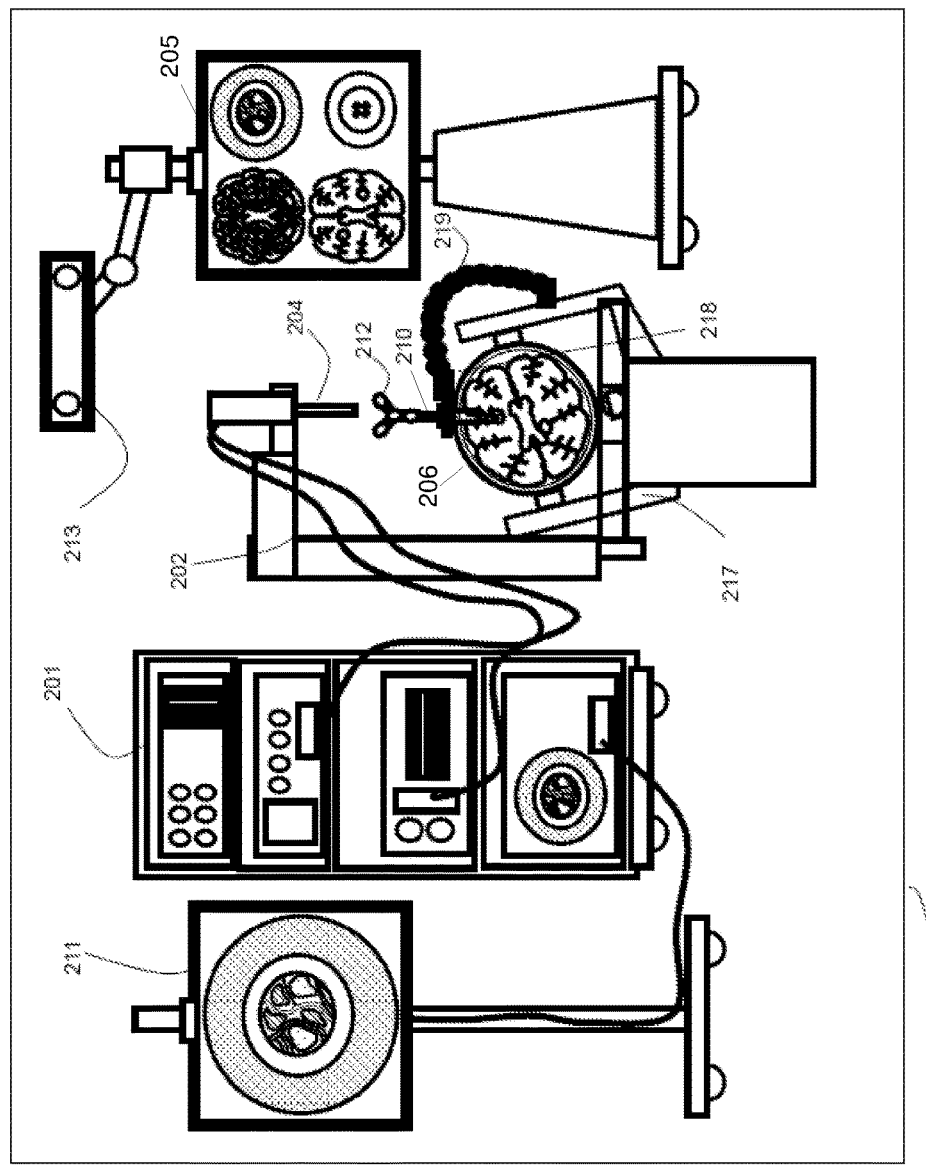
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
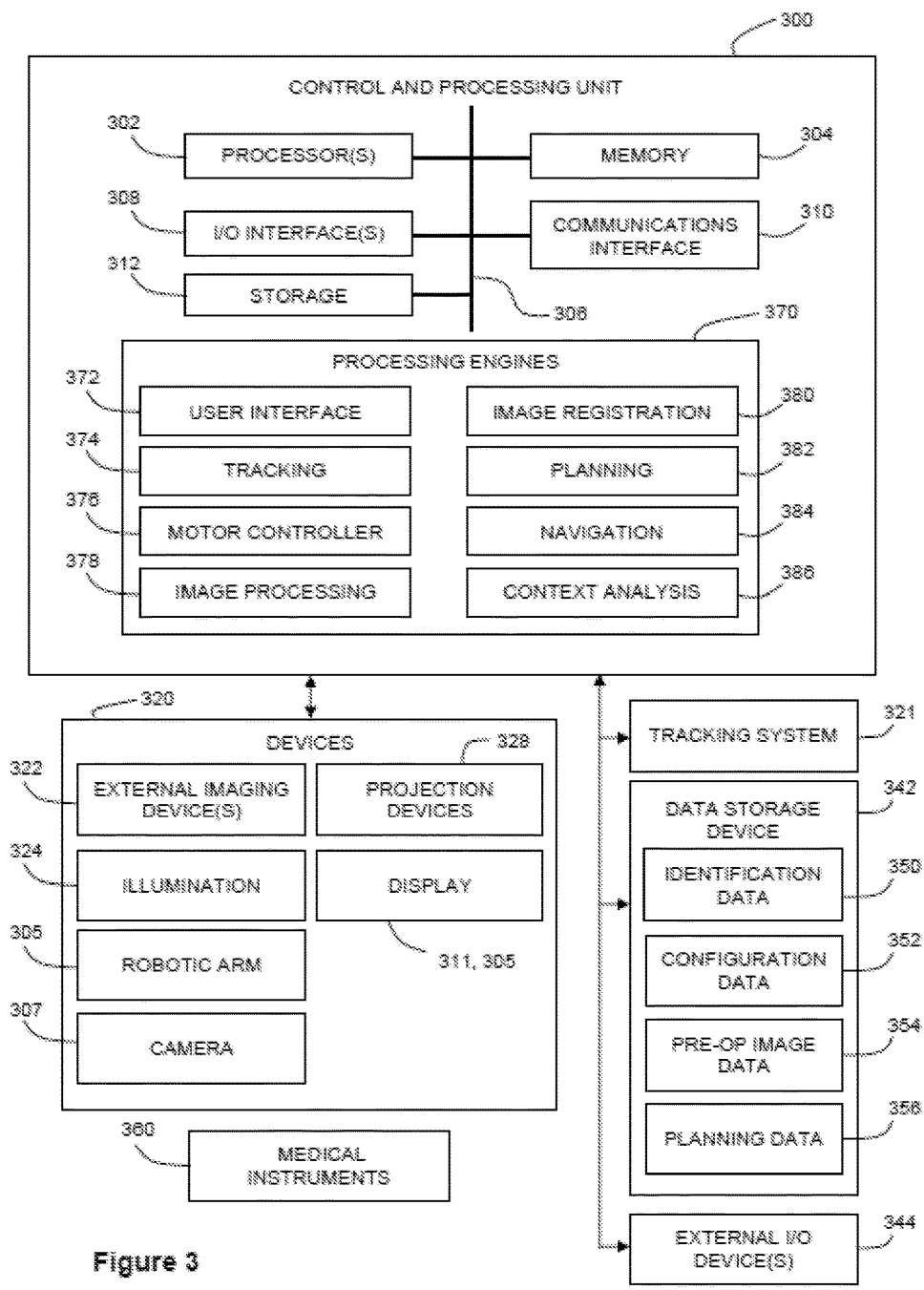
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
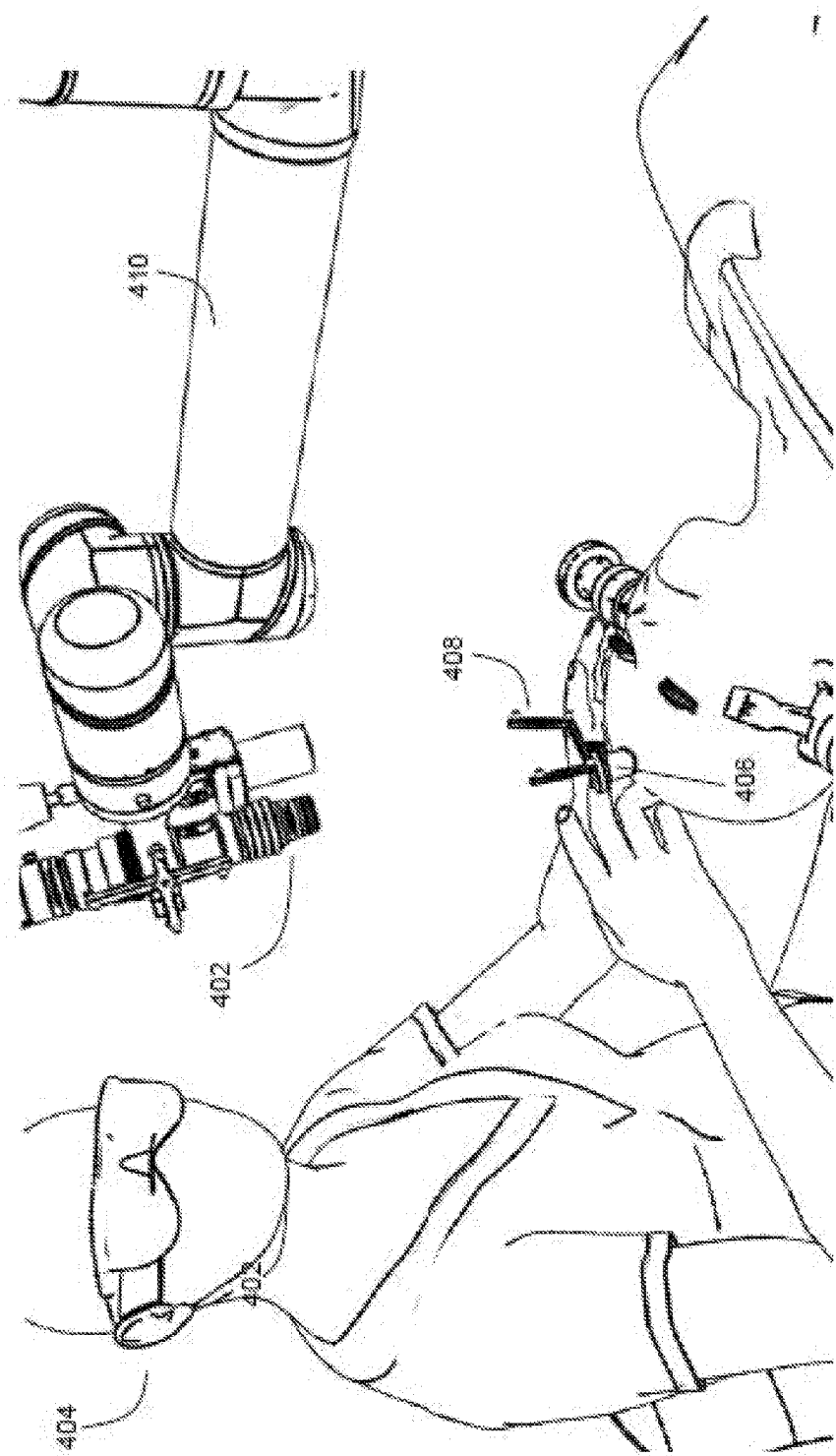
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
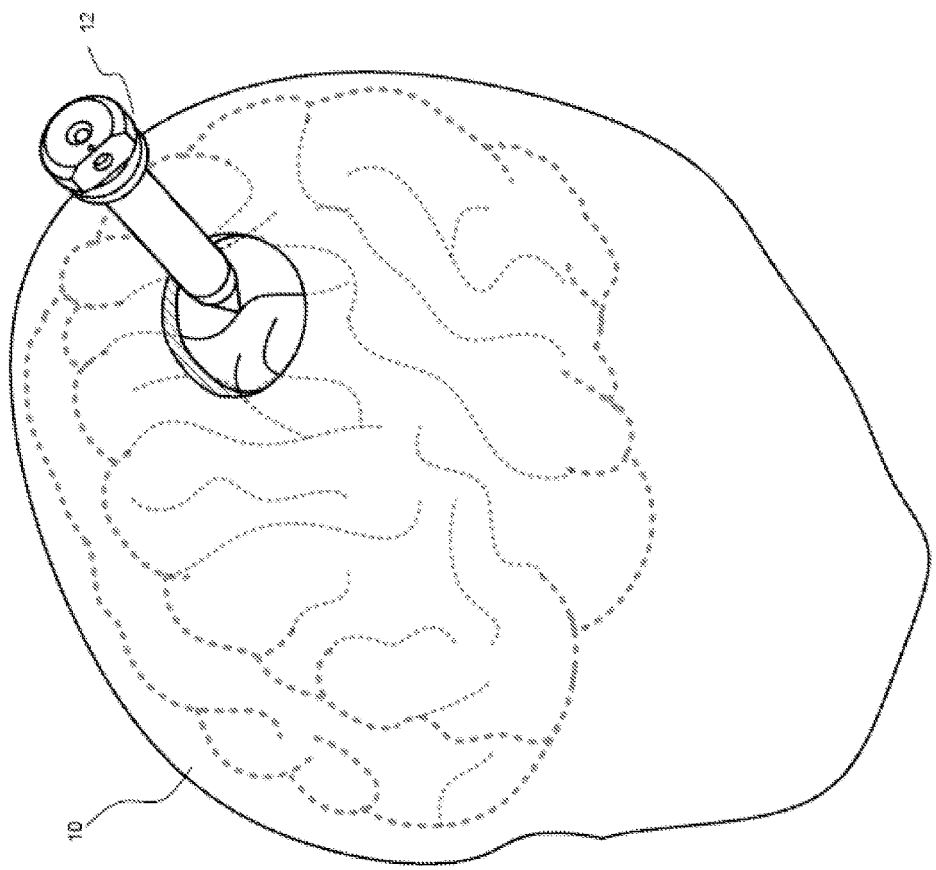
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Attention is next directed to FIG. 6, which depicts an example of a surgical tool that could be used with and/or in place of access port 12.

Specifically, FIG. 6 depicts a surgical camera system 600 comprising: a tunable iris 601 configured to automatically alternate between a first depth of field and a second depth of field larger than the first depth of field; one or more lenses 603 configured to collect light using tunable iris 601; a body 605 containing tunable iris 601 and at least a portion of one or more lenses 603; a sensor 607 configured to produce images from the light received from one or more lenses 603 and tunable iris 601; a video processing unit 609 configured to: produce an image stream from first images and second images produced by sensor 607 from the light received from one or more lenses 603 and tunable iris 601, the first images acquired at the first depth of field and the second images acquired at the second depth of field; and adjust one or more lighting parameters of the first images and the second images prior to producing the image stream; and, a display device 626 in communication with video processing unit 609, display device 626 configured to render the image stream. In some implementations, body 605 can be configured for use with a surgical port (such as access port 12), such that system 600 can be used for port surgery; however, in other implementations body 605 can be configured for use in open surgery. Either way, system 600 can be configured for use in one or more port surgery, open surgery, and the like.

As depicted, system 600 further comprises a video buffering unit 630 configured to one or more of buffer and sequence the first images and the second images prior to being streamed by video processing unit 609. In other words, video buffering unit 630 is in communication video processing unit 609 and can be used by video processing unit 609 to produce the image stream. Indeed, as depicted, video processing unit 609 and video buffering unit 630 are housed in a common housing 639, and video processing unit 609 and video buffering unit 630 together can comprise a computing device.

Also depicted in FIG. 6 is an optional tracking device 655 attached to a proximal end of housing 639. In other words, as depicted, system 600 optionally comprises tracking device 655 configured to be tracked by a navigation system.

Tracking device 655 is generally configured to be tracked by a navigation system external to system 600, for example a navigation system that is part of surgical system, such as that depicted in FIGS. 1 to 4. While not depicted housing 639 can further comprise a mount configured to removably attach tracking device 655 at a proximal end thereof (e.g. an end that is away from tissue being imaged). Tracking device 655 is generally positioned so that a camera, and the like, of a surgical navigation system may track a position of tracking device 655 and hence a relative position of distal end 650 of body 605. As depicted, tracking device 655 comprises four reflective spheres arranged in a configuration where each sphere is located at about a corner of a square. However, other numbers of spheres and other configurations are within the scope of present implementations. In particular or more of a number, arrangement, and configuration of such spheres may be selected to provide a given tracking accuracy, including, but not limited to, a tracking accuracy that is less than about half a diameter of a sensing array surface. However, tracking device 655 may include tracking devices other than reflective spheres. For example, in some implementations, tracking device 655 may include a flexible sheath configured to measure tip position deflection, for example deflection of a tip of the flexible sheath. Furthermore, system 600 can be adapted to include one or more tracking devices.

Furthermore, in some implementations, system 600 (other than display device 626) can comprise an optical scope similar to optical scope 204, which can be positioned with respect to a patient and/or tissue and/or a sample to be imaged using a device positioning system including, but not limited to, mechanical arm 202. Such positioning can occur using, in part, tracking device 655.

In any event, tunable iris 601 can comprise an electronically controlled iris with at least two positions: a first position comprising a first depth of field, and a second position comprising a second depth of field. For example, tunable iris 601 can comprise an adjustable diaphragm and one or more of a motor, a stepper motor, and the like, configured to adjust the diaphragm between the first depth of field and the second depth of field. Tunable iris 601 can be in communication with, and controlled by, video processing unit 609 and/or another processor (not depicted) so that video processing unit 609 and/or the another processor can control a depth of field of tunable iris 601 according to a sequence, as described in further detail below.

Figure 7:
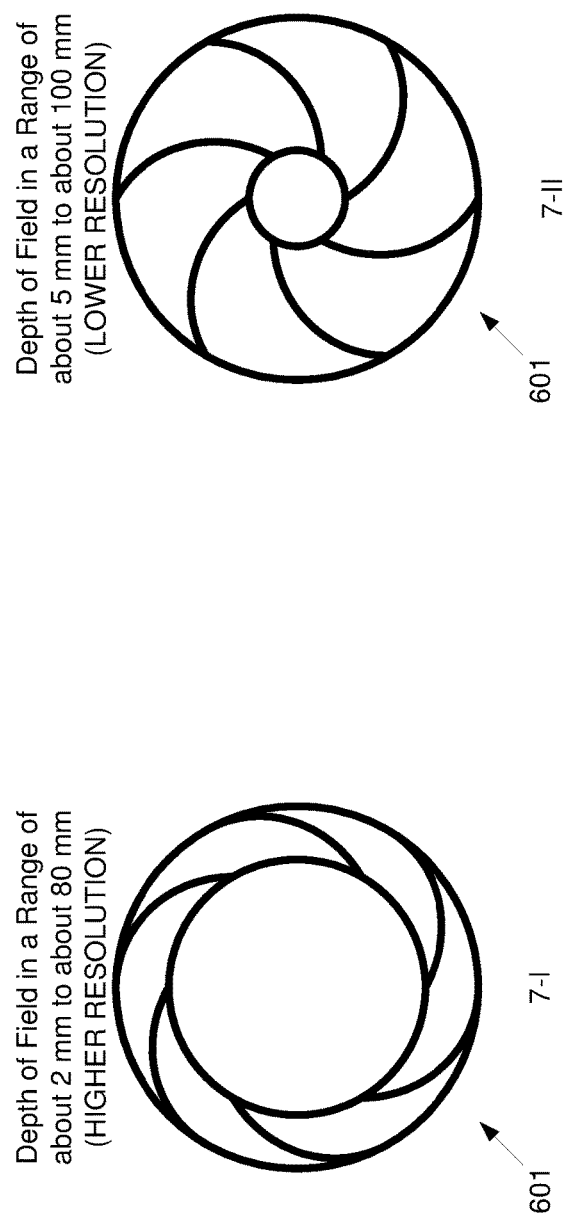
FIG. 7 depicts two positions of a tunable iris of the system of FIG. 6, according to non-limiting implementations.

For example, attention is briefly directed to FIG. 7 which depicts tunable iris 601 in a first position 7-I and a second position 7-II; in the first position 7-I, tunable iris 601 has a larger aperture compared to second position 7-II, and hence in the second position 7-II the depth of field will be larger than in the first position. FIG. 7 assumes that tunable iris 601 comprises a diaphragm adjustable between positions 7-I, 7-II; however other mechanisms for adjusting depth of field are within the scope of present implementations, including, but not limited to, a MEMS (microelectromechanical systems) based tunable iris, a liquid crystal tunable iris, a liquid tunable iris, and the like.

For example, as depicted, in first position 7-I, the depth of field is in a range of about 2 mm to about 80 mm, and in second position 7-II, the depth of field is in a range of about 5 mm to about 100 mm. While these ranges overlap, the selected depths of field for each position 7-I, 7-II will additionally meet a condition of the depth of field for position 7-II being larger than the depth of field for position 7-I.

While not depicted a motor, a stepper motor and the like can be used to change tunable iris 601 between the first position and the second position, for example by controlling a position of the diaphragm. In some implementations, the two positions 74, 7-II can be discrete positions: for example, a diaphragm (and the like) of tunable iris 601 can be configured to move between the two positions 74, 7-II without stopping in between and/or the diaphragm of tunable iris 601 can be configured to temporarily lock into place at each of the two positions 7-I, 7-II, moving when actuated by a motor, and/or the diaphragm of tunable iris 601 can be configured to spring between the two positions 7-I, 7-II when actuated, for example by a motor. Hence, tunable iris 601 can be configured to automatically alternate between a first depth of field and a second depth of field larger than the first depth of field under control of such a motor and/or other type of control apparatus compatible with tunable iris 601, which in turn can be controlled by video processing unit 609 and/or another processor.

It is further appreciate that tunable iris 601 can alternate between the first depth of field and the second depth of field according to a sequence. For example, tunable iris 601 can spend more time at one depth of field than another depth of field, depending on a number of images being acquired by sensor 607 at a given depth of field.

Returning to FIG. 6, one or more lenses 603 can be located between tunable iris 601 and sensor 607 and/or between tunable iris 601 and a distal end 650 of body 605. Furthermore, in the present specification following, the terms proximal end and distal end will be used to refer to respective ends of components, with a proximal end being an end that will be proximal a surgeon and the like, when system 600 is in use, and a distal end being an end that will be distal the surgeon, and/or directed towards tissue, a sample, a patient being operated on, and the like, when system 600 is in use. Hence, for example, body 605 comprises a proximal end and a distal end 650, distal end 650 configured for positioning adjacent tissue being imaged by tunable iris 601, for example as depicted in FIG. 10 described in more detail below.

System 600 can comprise any suitable number and arrangement of lenses that enables acquisition of images by tunable iris 601 and sensor 607. In particular, system 600 comprises an arrangement of lenses configured to focus light from a sample at a focusing plane onto sensor 607 via tunable iris 601, which controls the depth of field.

Body 605 can be generally configured for use with a surgical port, including, but not limited to, access port 12. For example, in some implementations, body 605 is configured for positioning relative to a surgical port so that system 600 can be used to image through the surgical port. In other implementations, body 605 can be configured for insertion into a surgical port and/or through a surgical port. However, in other implementations, body 605 can be configured for use with open surgery and/or both port surgery and open surgery.

Further while body 605 is depicted as cylindrical, in other implementations, body 605 can comprise other shapes and in particular elongated shapes. Furthermore, body 605 can be of a diameter that enables surgical tools to be inserted down a same surgical port so that system 600 can be used to image tissue being operated upon. In some implementations, body 605 can be adapted to include external clip, vias and the like for use with surgical tools so that body 605 can be used to assist positioning of the surgical tools in the surgical port.

Sensor 607 can comprise an electronic imaging sensor including, but not limited to a charge coupled device (CCD). In general, one or more lenses 603 focus light from a sample located at distal end 650 onto sensor 607 via tunable iris 601. Sensor 607 can acquires images which are received at video processing unit 609 and/or buffered at video buffering unit 630.

Video processing unit 609 can be implemented as a plurality of processors, including but not limited to one or more central processors ("CPUs"). Video processing unit 609 can further comprise one or more hardware processors and/or digital signal processors ("DSP"). Video processing unit 609 can be configured to communicate with video buffering unit 630 comprising a non-volatile storage unit (e.g. Erasable Electronic Programmable Read Only Memory ("EEPROM"), Flash Memory) and a volatile storage unit (e.g. random access memory ("RAM")). Programming instructions that implement the functional teachings of system 600 as described herein are typically maintained, persistently, in video buffering unit 630 and used by video processing unit 609 which makes appropriate utilization of volatile storage during the execution of such programming instructions.

Video processing unit 609 is further configured to communicate with display device 626, which comprises any suitable one of, or combination of, flat panel displays (e.g. LCD (liquid crystal display), plasma displays, OLED (organic light emitting diode) displays, capacitive or resistive touchscreens, CRTs (cathode ray tubes) and the like. In some implementations, display device 626 comprises a heads up display (HUD) device worn, for example, by a surgeon and the like.

In some implementations, system 600 and/or video processing unit 609 can include a reference clock, for example for determining when to control tunable iris 601 to a given depth of field, for example see FIG. 10 below.

While not depicted, in other implementations, system 600 can comprise one or more illumination sources to illuminate tissue from which images are being acquired; such illumination sources can be arranged to illuminate an area adjacent distal end 650 and can include, but are not limited to, light emitting diodes.

Attention is now directed to FIG. 8 which depicts a block diagram of a flowchart of a method 800 of controlling system 600 to acquire images at different depths of field, according to non-limiting implementations. In order to assist in the explanation of method 800, it will be assumed that method 800 is performed using system 600, including video processing unit 609 and/or another processor controlling system 600 including tunable iris 601 and sensor 607. Indeed, method 800 is one way in which system 600 can be configured. Furthermore, the following discussion of method 800 will lead to a further understanding of system 600, and its various components. However, it is to be understood that system 600 and/or method 800 can be varied, and need not work exactly as discussed herein in conjunction with each other, and that such variations are within the scope of present implementations.

Regardless, it is to be emphasized, that method 800 need not be performed in the exact sequence as shown, unless otherwise indicated; and likewise various blocks may be performed in parallel rather than in sequence; hence the elements of method 800 are referred to herein as "blocks" rather than "steps". It is also to be understood, however, that method 800 can be implemented on variations of system 600 as well.

At block 801, video processing unit 609, and the like, controls tunable iris 601 to change depths of field, for example, in a sequence.

At block 802, sensor 607 acquires images at the different depths of field, for example, in the sequence of block 801.

At an optional block 803, images from sensor 607 can be buffered at video buffering unit 630.

At block 805, video processing unit 609 produces an image stream from images acquired by sensor 607, for example, images buffered at video buffering unit 630 at block 803. The image stream can comprises images acquired by sensor 607 in a sequence At block 807, video processing unit 609 outputs the image stream as video to display device 626.

Method 800 will now be described with reference to FIGS. 9 to 10.

Attention is next directed to FIG. 9 which depicts a time sequence 900 for controlling tunable iris 601 using a reference clock. In particular tunable iris 601 can be configured to automatically alternate between the first depth of field and the second depth of field according to time sequence 900 generated using the reference clock. In particular, the first images and the second images can be acquired in association with alternating pulses of the time sequence 900.

For example, the first row of time sequence 900 depicts time pulses T1, T2 . . . Tn . . . generated by the reference clock. As depicted, at a rising edge of first time pulse T1, tunable iris 601 is controlled (e.g. at block 801 of method 800) to a position where a depth of field is low but where higher resolution images can be acquired (e.g. position 7-I), and first high resolution image $I_{h/1}$ is acquired at sensor 607 (e.g. at block 802 of method 800); image $I_{h/1}$ can optionally be buffered at video buffering unit 630 (e.g. at block 803 of method 800). Video processing unit 609 can receive image $I_{h/1}$ (e.g. at block 805 of method 800), from sensor 607 and/or video buffering unit 630, and output image $I_{h/1}$ as a video frame $V_{h/1}$ to display device 626 at a falling edge of time pulse T1 (e.g. at block 807 of method 800). In other words, acquisition of image $I_{h/1}$ is triggered by T1 up rise edge and the first video frame $V_{h/1}$ can be rendered at display device 626 at T1 time edge down.

Similarly, at a rising edge of second time pulse T2, tunable iris 601 is controlled (e.g. at block 801 of method 800) to a position where a depth of field is high but where lower resolution images can be acquired (e.g. position 7-II), and first low resolution image $I_{lh1}$ is acquired at sensor 607 (e.g. at block 802 of method 800); image $I_{lh1}$ can optionally be buffered at video buffering unit 630 (e.g. at block 803 of method 800). Video processing unit 609 can receive image $I_{lh1}$ (e.g. at block 805 of method 800), from sensor 607 and/or video buffering unit 630, and output image $I_{lh1}$ as a video frame $V_{lh1}$ to display device 626 at a falling edge of time pulse T2 (e.g. at block 807 of method 800). In other words, acquisition of image $I_{lh1}$ is triggered by T2 up rise edge and the second video frame $V_{lh1}$ can be rendered at display device 626 at T2 time edge down.

At time pulse T3, acquisition of a second high resolution image $I_{h/2}$ occurs, and at time pulse T4, acquisition of a second low resolution image $I_{lh2}$ occurs, with corresponding video frames $V_{h/2}, V_{lh2}$ rendered at display device 626 at T3 and T4 time edges down. Hence, the image stream comprises video frames of a video stream.

In other words, method 800 can repeat as needed to provide a real-time rendering of the image stream at display device 626.

In any event, this sequence repeats to output video to display device 626. In other words, as depicted in FIG. 9, a video stream output to display device 626 by video processing unit 609 comprises an image stream that alternates between images acquired at the first depth of field and the second depth of field of tunable iris 601.

This is further depicted in FIG. 10, which is substantially similar to FIG. 6, with like elements having like numbers, however system 600 is depicted in use imaging tissue 1001. Hence, it is assumed in FIG. 10, that distal end 650 has been positioned using a robotic arm of a device positioning system (for example mechanical arm 202). In particular the two positions of tunable iris 601 are depicted in stippled lines corresponding to positions 7-I, 7-II described above. Furthermore, sensor 607 is depicted as acquiring images $I_{hln}, I_{lhn}$ at the respective depths of field of each of positions 7-I, 7-II, which are optionally buffered at video buffering unit 630. Images $I_{hln}, I_{lhn}$ are received at, and processed by video processing unit 609 to merge images $I_{hln}, I_{lhn}$ in a video stream, for example in video frames images $V_{hln}, V_{lhn}$, which are received at display device 626 and rendered at display device 626.

Hence, the image stream, as represented by the video stream depicted in FIGS. 9 and 10 comprise images acquired at the first depth of field and the second depth of field rendered in one or more given sequences. Indeed, while in FIGS. 9 and 10, the images at the first depth of field and the second depth of field of tunable iris 601 are depicted as alternating between the images at the first depth of field and the second depth, one after the other, other sequences are within the scope of present implementations. For example, if "1" represents an image acquired at a first depth of field and "2" represents an image acquired at a second depth of field, in FIGS. 9 and 10 the given sequences comprises: 1212121212 . . . . However, a sequence 111121112 . . . and/or a sequence 112112112 . . . are also within the scope of present implementations. Indeed, any sequence where some alternation occurs between images between the images at the first depth of field and the second depth are within the scope of present implementations.

In particular a given sequence can be selected, and the first depth of field and the second depth of field can be selected, so that the image stream results in a three dimensional effect at display device 626 when the image stream is rendered thereon. In other words, alternation between the images at the two depths of field can result in a viewer seeing different depth information for images of tissue 1001, which can result in a pseudo three-dimensional effect. For such an effect to occur, in some implementations, the frame rate of the video stream is greater than or equal to about 20 frames per second and in particular greater than or equal to about 60 frames per second. While the second images have a smaller resolution that the first images (i.e. the second images at the larger depth of field have a smaller resolution than the first images at the smaller depth of field), such differences in resolution tend to be ignored by the brain of a user at these frame rates.

Such rendering of image stream at a display device 626, which is viewed by both eyes of a surgeon and/or a viewer, is in contrast to a binocular camera which provides images with different depth information for each eye of a viewer, which are then merged within the brain of the viewer, but can lead to eye fatigue and/or headaches.

While not depicted, in some implementations, video processing unit 609 can process images $I_{hln}, I_{lhn}$ to adjust for differences in image parameters. For example, as already discussed, each of image stream $I_{hln}, I_{lhn}$ can be acquired at different resolutions; hence, in some implementations, video processing unit 609 can sharpen lower resolution images using video and/or image processing techniques, to attempt to bring the lower resolution images closer in resolution to the higher resolution images.

Furthermore, image stream $I_{hln}, I_{lhn}$ will generally be acquired under different lighting conditions which can occur inherently as tunable iris 601 changes between depths of field. Hence, one image stream $I_{hln}, I_{lhn}$ can be darker or brighter than the other of the image stream $I_{hln}, I_{lhn}$, which can lead to artifacts in the video stream and/or eye fatigue. As such, video processing unit 609 can be further configured to adjust one or more lighting parameters of the first images and the second images prior to producing the image stream by one or more of: balancing respective brightness of one or more of the first images and the second images; balancing respective gain values of one or more of the first images and the second images; and, performing brightness matching on one or more of the first images and the second images prior to producing the image stream.

In other words, in these implementations, video processing unit 609 attempts to balance the relative brightness of image stream $I_{hln}, I_{lhn}$.

Further, a surgical camera system is provided that includes a tunable iris that can be controlled between two depths of field, and images acquired at each depth of field are incorporated into an image stream and output to a display device, for example in a video stream, so that a surgeon can view the image stream with both eyes. In particular, such a system can be less expensive than a binocular system as only one sensor and one lens system is used. Furthermore, as image stream including images at the different depths of field are viewed by both eyes, eye fatigue can be reduced.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A surgical camera system comprising:
  a tunable iris configured to automatically alternate between a first depth of field and a second depth of field larger than the first depth of field;
  one or more lenses configured to collect light using the tunable iris; a body containing the tunable iris and at least a portion of the one or more lenses;
  a sensor configured to produce images from the light received from the one or more lenses and the tunable iris;
  a video processing unit configured to: produce a video stream at a frame rate that is greater than or equal to about 20 frames per second from first images and second images produced by the sensor from the light received from one or more lenses and the tunable iris, the first images acquired at the first depth of field and the second images acquired at the second depth of field; and adjust one or more lighting parameters of the first images and the second images prior to producing the video stream, the video stream comprising video frames that alternate between the first images acquired at the first depth of field and the second images acquired at the second depth of field; and,
  a display device in communication with the video processing unit, the display device configured to render the video stream, the first depth of field and the second depth of field selected so that the video stream results in a three dimensional effect at the display device when the video stream is rendered thereon.

2. The surgical camera system of claim 1, further comprising a video buffering unit configured to one or more of buffer and sequence the first images and the second images prior to being streamed by the video processing unit.

3. The surgical camera system of claim 1, wherein the image stream comprises images acquired at the first depth of field and the second depth of field rendered in one or more given sequences.

4. The surgical camera system of claim 1, wherein the first depth of field is in a range of about 5 mm to about 100 mm.

5. The surgical camera system of claim 1, wherein the second depth of field is in a range of about 2 mm to about 80 mm.

6. The surgical camera system of claim 1, wherein the second images have a smaller resolution than the first images.

7. The surgical camera system of claim 1, further comprising a reference clock, the tunable iris configured to automatically alternate between the first depth of field and the second depth of field according to a time sequence generated using the reference clock.

8. The surgical camera system of claim 7, wherein the first images and the second images are acquired in association with alternating pulses of the time sequence.

9. The surgical camera system of claim 1, wherein the display device comprises a heads up display (HUD) device.

10. The surgical camera system of claim 1, wherein the video processing unit is further configured to adjust one or more lighting parameters of the first images and the second images prior to producing the image stream by one or more of: balancing respective brightness of one or more of the first images and the second images; balancing respective gain values of one or more of the first images and the second images; and, performing brightness matching on one or more of the first images and the second images prior to producing the image stream.

11. The surgical camera system of claim 1, wherein the body comprises a proximal end and a distal end, the distal end configured for positioning adjacent tissue being imaged by the one or more lenses and the tunable iris.

12. The surgical camera system of claim 1, wherein the body is configured for use with a surgical port.

13. The surgical camera system of claim 1, further comprising a tracking device configured to be tracked by a navigation system.

* * * * *